United States Patent
Prieditis et al.

(10) Patent No.: US 11,521,744 B1
(45) Date of Patent: Dec. 6, 2022

(54) MACHINE LEARNING SYSTEM FOR GENERATING PREDICTIONS ACCORDING TO VARIED ATTRIBUTES

(71) Applicant: Cigna Intellectual Property, Inc., Wilmington, DE (US)

(72) Inventors: Armand E. Prieditis, Arcata, CA (US); John E. Paton, Raleigh, NC (US)

(73) Assignee: Cigna Intellectual Property, Inc., Wilmington, DE (US)

( * ) Notice: Subject to any disclaimer, the term of this patent is extended or adjusted under 35 U.S.C. 154(b) by 308 days.

(21) Appl. No.: 16/731,316

(22) Filed: Dec. 31, 2019

Related U.S. Application Data (60) Provisional application No. 62/862,845, filed on Jun. 18, 2019.

(51) Int. Cl.
| | | |
|---|---|---|
| *G16H 50/20* | (2018.01) | |
| *G16H 50/30* | (2018.01) | |
| *G06N 20/00* | (2019.01) | |
| *G06F 17/16* | (2006.01) | |
| *G06F 17/18* | (2006.01) | |
| *G16H 40/67* | (2018.01) | |

(52) U.S. Cl.
CPC ............ *G16H 50/20* (2018.01); *G06F 17/16* (2013.01); *G06F 17/18* (2013.01); *G06N 20/00* (2019.01); *G16H 50/30* (2018.01)

(58) Field of Classification Search
CPC ........ G16H 50/20; G16H 50/30; G16H 40/67; G06F 17/16; G06F 17/18; G06N 20/00; G06N 5/04; G06Q 10/04; G06Q 50/24; G16Z 99/00
USPC ...................................................... 705/2, 3
See application file for complete search history.

(56) References Cited

U.S. PATENT DOCUMENTS

| | | |
|---|---|---|
| 8,412,652 B2 | 4/2013 | Yu |
| 9,306,947 B2 | 4/2016 | Kolbly |
| 9,928,574 B2 | 3/2018 | Gandolph |
| 9,971,578 B2 | 5/2018 | Duffy |

(Continued)

OTHER PUBLICATIONS

IBM, Customer Intelligence & Next Best Action, The "Art of the Possible" and "Best Practices", https://www.IBM.com/cloud-computing/NewCustomerIntelligencev33v1short.pdf, at least as early as Apr. 17, 2019.

(Continued)

*Primary Examiner* — Fonya M Long
*Assistant Examiner* — Alaaeldin M Elshaer
(74) *Attorney, Agent, or Firm* — Miller Johnson (57) ABSTRACT

A method includes maintaining sets of values for mutable and immutable attributes. Each outcome model of a set of outcome models generates a predicted likelihood of an outcome in response to at least one immutable attribute value and at least one mutable attribute value. A prediction request specifies a first outcome, values for at least one immutable attribute, and values for at least one mutable attribute. The method includes, in response, selecting a group of the sets, where each has values for the immutable attributes that match those of the prediction request. The method includes determining a conditional covariance matrix for the group of sets and then generating a deviation model. The method includes sampling the deviation model to generate sets of mutable attribute values. The method includes, for each of the sets of mutable attribute values, generating, using a selected outcome model, a likelihood of the first outcome occurring.

20 Claims, 4 Drawing Sheets

(56) References Cited

U.S. PATENT DOCUMENTS

| | | |
|---|---|---|
| 10,320,879 B2 | 6/2019 | Nekrestyanov |
| 10,431,337 B2 | 10/2019 | Allen |
| 10,431,338 B2 | 10/2019 | Allen |
| 2017/0140288 A1 | 5/2017 | Pourshahid |
| 2017/0262809 A1 | 9/2017 | Martin |
| 2020/0151582 A1 | 5/2020 | Sharp |

OTHER PUBLICATIONS

Priest, Delivering Next Best Action with Artificial Intelligence, https://www.datarobot.com/blog/delivering-next-best-action-with-artificial-intelligence, Apr. 10, 2018.

MACHINE LEARNING SYSTEM FOR GENERATING PREDICTIONS ACCORDING TO VARIED ATTRIBUTES

CROSS-REFERENCE TO RELATED APPLICATIONS

This application claims the benefit of U.S. Provisional Application No. 62/862,845 filed Jun. 18, 2019. The entire disclosure of the application referenced above is incorporated by reference.

FIELD

The present disclosure relates to machine learning and more particularly to machine-learning-based prediction generation based on immutable and mutable values.

BACKGROUND

Machine learning has seen enormous growth over the last decade, particularly in business and healthcare applications. A typical application of machine learning is to generate predictions based on historical data. The historical data may include mutable and immutable attribute values of entities—for example, patients. An immutable attribute is an attribute of an entity that cannot be altered. A patient's age or genetic profile are examples of immutable attributes. A mutable attribute is an attribute of an entity that may be altered. An entity's weight, body mass index (BMI), cholesterol, VO2 max (the maximum rate of oxygen consumption during incremental exercise), and tobacco usage are examples of mutable attributes. However, machine learning models traditionally fail to account for this distinction.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A computer-implemented method includes maintaining an attribute data store that includes a plurality of sets of values for mutable attributes and immutable attributes. The method includes maintaining a set of outcome models. Each outcome model of the set of outcome models generates a predicted likelihood of a respective outcome in response to at least one immutable attribute value and at least one mutable attribute value. The method includes receiving a prediction request that specifies a first outcome, a set of values for at least one immutable attribute, and a set of values for at least one mutable attribute. The method includes, in response to the prediction request selecting a group of sets from the plurality of sets of the attribute data store. Each set in the group of sets has values for the immutable attributes that match the set of values for the at least one immutable attribute in the prediction request. The method includes determining a conditional covariance matrix for the group of sets. The method includes generating a deviation model based on the conditional covariance matrix. The method includes sampling the deviation model to generate a plurality of sets of mutable attribute values. The method includes selecting one of the set of outcome models. The method includes, for each of a subset of the plurality of sets of mutable attribute values, generating, using the selected outcome model and the set of values for the at least one immutable attribute of the prediction request, a respective likelihood of the first outcome occurring. The method includes, based on the respective likelihoods, selectively generating a message with an action recommendation. The method includes automatically transmitting the message to a user associated with the prediction request.

In other features, the conditional covariance matrix is calculated according to $$\hat{\Sigma}_a = \Sigma_a - \Sigma_c \Sigma_b^{-1} \Sigma_c^T.$$

$\hat{\Sigma}_a$ is the conditional covariance matrix, $\Sigma_a$ is a covariance matrix associated with the values for the mutable attributes in the group of sets, $\Sigma_b^{-1}$ is an inverse of a covariance matrix associated with the values for the immutable attributes in the group of sets, $\Sigma_c$ is a covariance matrix of the values for the mutable attributes in the group of sets crossed with the values for the immutable attributes in the group of sets, and $\Sigma_c^T$ is the transpose of $\Sigma_c$.

In other features, the subset is increased until a predetermined number is reached. In other features, the deviation model is generated based on the conditional covariance matrix as well as a mean mutable values vector. In other features, the set of values for the at least one mutable attribute of the prediction request is used as the mean mutable values vector. In other features, the deviation model represents a multivariate Gaussian distribution. In other features, the first outcome is a medical outcome including at least one of a medical diagnosis or a prescribed procedure.

In other features, each of the plurality of sets of values includes a time horizon. The prediction request includes a first time horizon. Each set in the group of sets has a time horizon that corresponds to the first time horizon. In other features, each outcome model of the set of outcome models generates the predicted likelihood of the respective outcome in response to the at least one immutable attribute value, the at least one mutable attribute value, and the time horizon. In other features, the time horizon is measured in months.

In other features, the immutable attributes include age and the mutable attributes include at least one of body mass index (BMI), tobacco usage, cholesterol level, and VO2 max. In other features, the selected outcome model is selected according to the first outcome of the prediction request.

A system includes memory hardware configured to store instructions and processing hardware configured to execute the instructions stored by the memory hardware. The instructions include maintaining an attribute data store that includes a plurality of sets of values for mutable attributes and immutable attributes. The instructions include maintaining a set of outcome models. Each outcome model of the set of outcome models generates a predicted likelihood of a respective outcome in response to at least one immutable attribute value and at least one mutable attribute value. The instructions include receiving a prediction request that specifies a first outcome, a set of values for at least one immutable attribute, and a set of values for at least one mutable attribute. The instructions include, in response to the prediction request, selecting a group of sets from the plurality of sets of the attribute data store. Each set in the group of sets has values for the immutable attributes that match the set of values for the at least one immutable attribute in the prediction request. The instructions include determining a conditional covariance matrix for the group of sets. The instructions include generating a deviation model based on the conditional covariance matrix. The instructions include sampling the deviation model to generate a plurality of sets of mutable attribute values. The instructions include selecting one of the set of outcome models. The instructions include, for each of a subset of the plurality of sets of mutable attribute values, generating, using the selected outcome model and the set of values for the at least one immutable attribute of the prediction request, a respective likelihood of the first outcome occurring. The instructions include, based on the respective likelihoods, selectively generating a message with an action recommendation. The instructions include automatically transmitting the message to a user associated with the prediction request.

In other features, the deviation model is generated based on the conditional covariance matrix as well as a mean mutable values vector. The deviation model represents a multivariate Gaussian distribution. In other features, the set of values for the at least one mutable attribute of the prediction request is used as the mean mutable values vector.

In other features, each of the plurality of sets of values includes a time horizon. The prediction request includes a first time horizon. Each set in the group of sets has a time horizon that corresponds to the first time horizon. In other features, each outcome model of the set of outcome models generates the predicted likelihood of the respective outcome in response to the at least one immutable attribute value, the at least one mutable attribute value, and the time horizon.

A non-transitory computer-readable medium stores processor-executable instructions. The instructions include maintaining an attribute data store that includes a plurality of sets of values for mutable attributes and immutable attributes. The instructions include maintaining a set of outcome models. Each outcome model of the set of outcome models generates a predicted likelihood of a respective outcome in response to at least one immutable attribute value and at least one mutable attribute value. The instructions include receiving a prediction request that specifies a first outcome, a set of values for at least one immutable attribute, and a set of values for at least one mutable attribute. The instructions include, in response to the prediction request, selecting a group of sets from the plurality of sets of the attribute data store. Each set in the group of sets has values for the immutable attributes that match the set of values for the at least one immutable attribute in the prediction request. The instructions include determining a conditional covariance matrix for the group of sets. The instructions include generating a deviation model based on the conditional covariance matrix. The instructions include sampling the deviation model to generate a plurality of sets of mutable attribute values. The instructions include selecting one of the set of outcome models. The instructions include, for each of a subset of the plurality of sets of mutable attribute values, generating, using the selected outcome model and the set of values for the at least one immutable attribute of the prediction request, a respective likelihood of the first outcome occurring. The instructions include, based on the respective likelihoods, selectively generating a message with an action recommendation. The instructions include automatically transmitting the message to a user associated with the prediction request.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

In the drawings, reference numbers may be reused to identify similar and/or identical elements.

DETAILED DESCRIPTION

Introduction

Although a prediction may be based on both mutable and immutable attribute values of a subject, the prediction traditionally does not indicate how changes to the subject's mutable attributes may affect the prediction—in other words, what action could or should be taken to reach or avoid a particular outcome. Often, changing more than one mutable attribute may result in the most desirable outcome.

System

Figure 1:
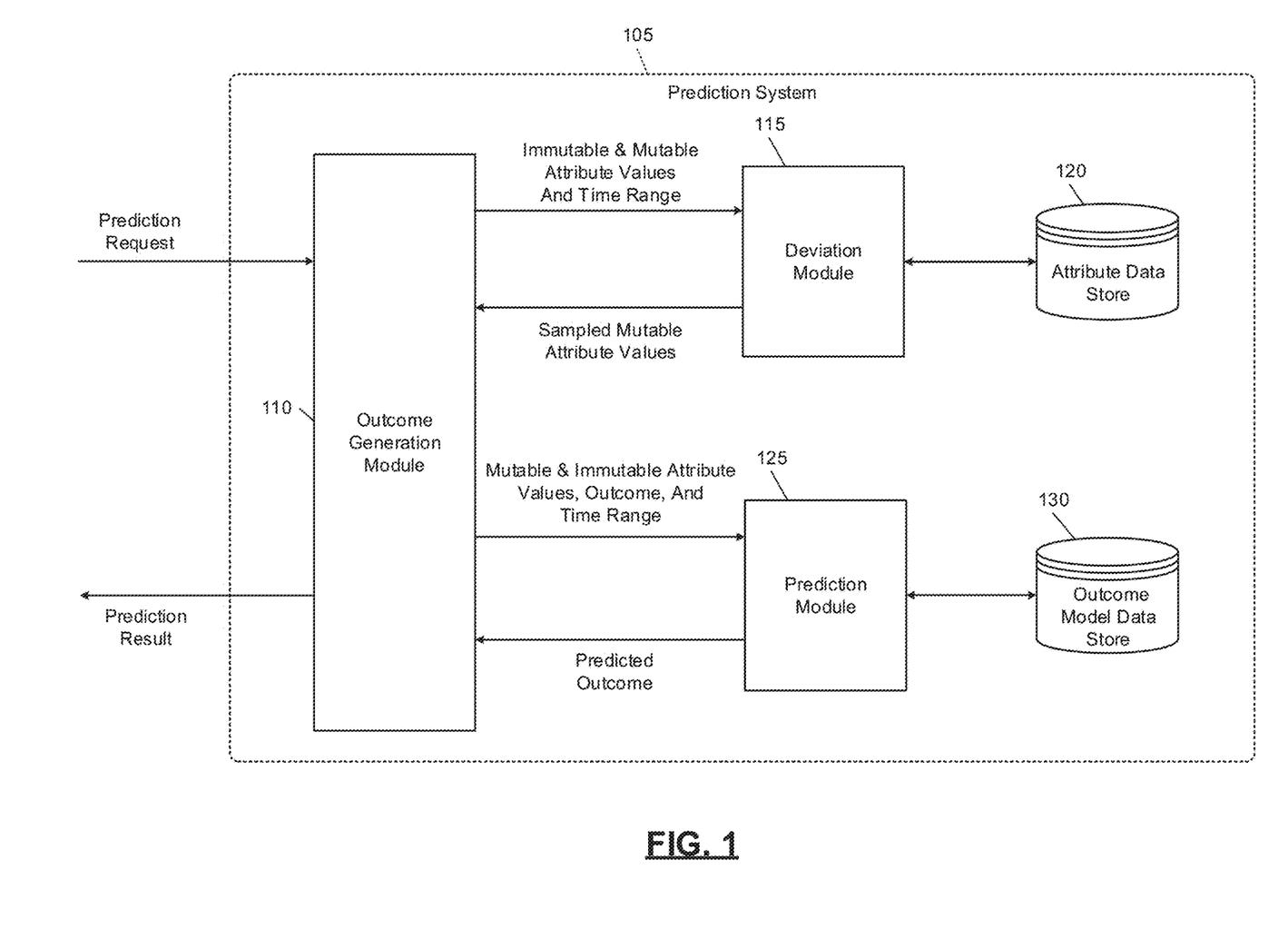
FIG. 1 is a functional block diagram of an example implementation of a system according to the principles of the present disclosure.

In FIG. 1, an prediction system 105 receives a prediction request that includes (i) immutable and mutable attribute values associated with a subject, (ii) an outcome, and (iii) a time range associated with the outcome. As an example, the outcome may be hip or knee surgery and the time range may be 12 months (that is, within the next year). In various implementations, the outcome may be any other medical diagnosis (such as a diagnosis of metabolic syndrome) or prescribed procedure (such as surgery or initiation of a blood pressure medication regimen).

In response to receiving a prediction request, the prediction system 105 outputs a set of predicted outcomes based on the immutable attribute values associated with the subject and a variety of possible mutable attribute values, including the mutable attribute values currently associated with the subject. The outputted predicted outcomes may be used to determine a recommended action for the subject to take to help the subject achieve a preferred outcome—for example, avoiding surgery.

The prediction system 105 includes an outcome generation module 110. The outcome generation module 110 is configured to receive the prediction request. In some implementations, the outcome generation module 110 may receive the prediction request directly from a user device—such as a computer or smartphone (not shown). In other implementations, the outcome generation module 110 may receive the prediction request from another source.

The prediction system 105 further includes a deviation module 115 and a prediction module 125. In response to receiving the prediction request, the outcome generation module 110 provides the deviation module 115 with the immutable and mutable attribute values and the time range included in the prediction request.

The deviation module 115 generates a deviation model associated with the received request based on data stored in an attribute data store 120. The attribute data store 120 includes a plurality of sets of mutable and immutable attribute values. Each value set of the plurality of sets is associated with a different subject. The deviation module 115 determines a conditional covariance matrix ($\hat{\Sigma}_a$) for a selected set of values sets. The selected set of values sets includes each value set stored in the attribute data store 120 that includes immutable attribute values that match the values received from the outcome generation module 110 and that correspond to the time range received from the outcome generation module 110. The time range may be specified in, for example, days, months, or years. A first time range may correspond to a second time range if the difference between the two time ranges is less than a predetermined threshold, such as 10%.

The deviation module 115 may use Equation 1 to generate the conditional covariance matrix ($\hat{\Sigma}_a$).

$$\hat{\Sigma}_a = \Sigma_a - \Sigma_c \Sigma_b^{-1} \Sigma_c^T \quad (1)$$

$\Sigma_a$ is the covariance matrix associated with the mutable attributes in the selected set of value sets. $\Sigma_b$ is the covariance matrix associated with the immutable attributes in the selected value sets. $\Sigma_c$ is the covariance matrix of the mutable attributes in the selected values sets crossed with the immutable attributes in the selected value sets. $\Sigma_c^T$ is the transpose of $\Sigma_c$ and $\Sigma_b^{-1}$ is the inverse of $\Sigma_b$. The deviation module 115 may store the determined conditional covariance matrix ($\hat{\Sigma}_a$) in the attribute data store 120. In some implementations, the deviation module 115 may retrieve a conditional covariance matrix stored in the attribute data store 120 rather than generating the conditional covariance matrix based on data stored in attribute data store 120.

The deviation module 115 creates a deviation model that (i) is associated with the received immutable and mutable attribute values and (ii) outputs a set of mutable attribute values. The deviation model includes the conditional covariance matrix and a mean mutable values vector. The deviation module 115 uses the mutable attribute values received from the outcome generation module 110 as the mean mutable values vector. The deviation model generated by the deviation module 115 represents a multivariate Gaussian distribution that may be sampled to produce a set of likely mutable attribute values.

Since the deviation model is learned from data stored in the attribute data store 120 that represents the general population, the samples obtained from the deviation model are limited to only those deviations that are possible for a given subject based on knowledge of what is possible in the general population. For example, if the mutable attribute values in the prediction request correspond to various lifestyle changes for the subject, the deviation model might produce deviations from the current lifestyle of the subject based on demographics and health history of the subject.

The outcome generation module 110 provides the prediction module 125 with a set of immutable and mutable values. The outcome generation module 110 may provide either the mutable attribute values included in the prediction request or the sampled mutable attribute values received from the deviation module 115 as the set of mutable values. The immutable attribute values may be included in the prediction request as the set of immutable values. The outcome generation module 110 also provides the prediction module 125 with the outcome and time range included in the prediction request.

The prediction module 125 selects a machine-learned outcome model that corresponds to the received set of immutable values, mutable values, outcome, and time range. For example, the prediction module may load an outcome model stored in an outcome model data store 130 that accepts the set of immutable and mutable values received from the outcome generation module 110 as inputs and outputs a probability of the received outcome occurring during the received time range. Each outcome model stored in the outcome model data store 130 is a machine-learned model trained using historical data.

The prediction module 125 uses the selected outcome model to determine the probability of the received outcome based on the set of immutable and mutable values received from the outcome generation module 110. The prediction module 125 provides the determined probability to the outcome generation module 110. The outcome generation module 110 stores the received probability and the associated set of mutable values as a predicted outcome.

The outcome generation module 110 outputs the stored predicted outcomes as the result of the prediction request. For example, the outcome generation module 110 may output the stored predicted outcomes after the outcome generation module 110 has performed a predetermined number of cycles. Each cycle includes obtaining sampled mutable attribute values from the deviation module 115, providing the sampled values to the prediction module 125, and storing the received probability and associated set of mutable values.

Flowchart

Figure 2:
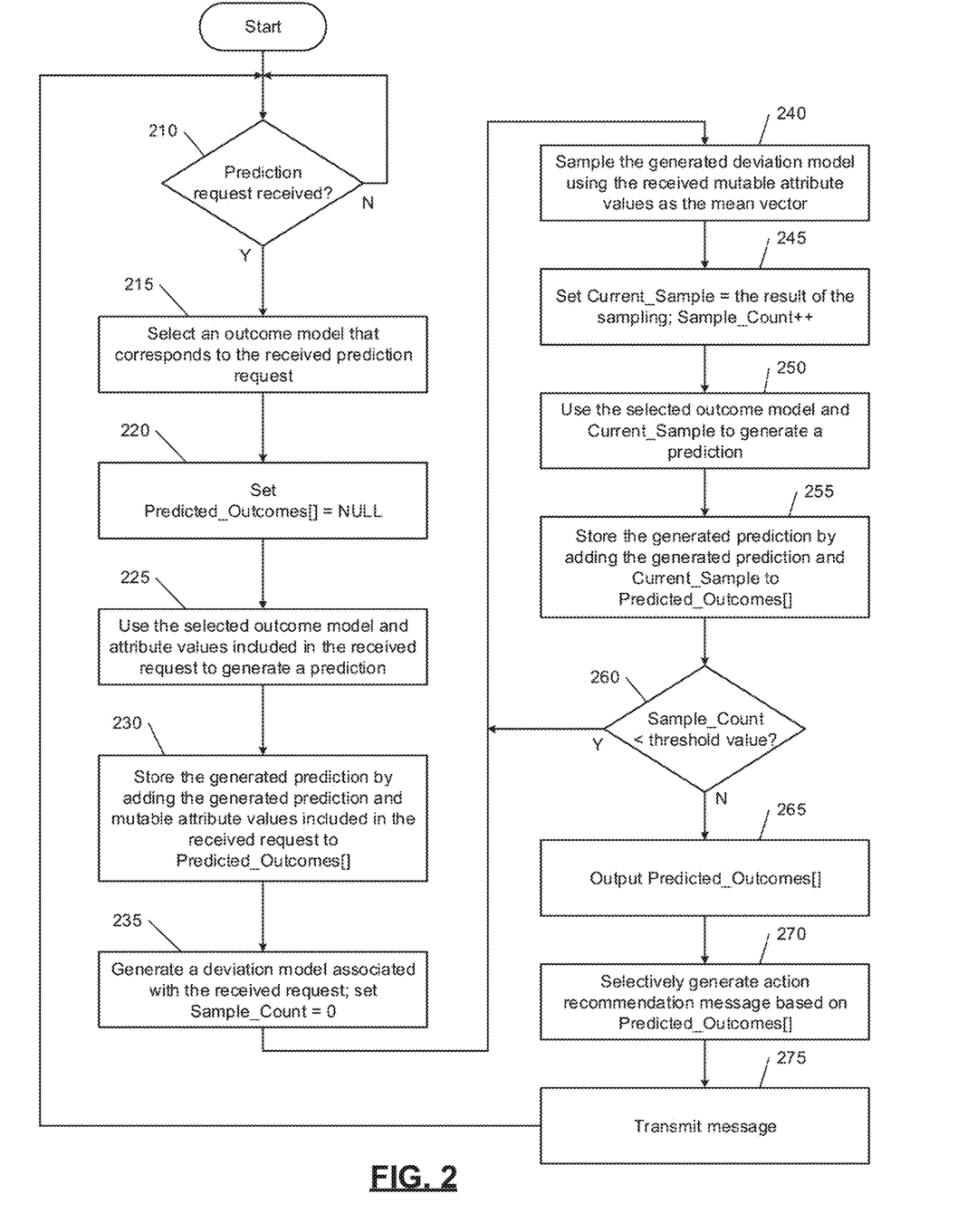
FIG. 2 is a flowchart of example request processing according to the principles of the present disclosure.

In FIG. 2, processing—for example, by the prediction system 105—of a prediction request begins at 210. At 210, control determines whether a prediction request has been received. If so, control transfers to 215; otherwise, control remains at 210. The prediction request includes (i) values of mutable and immutable attributes of a subject, (ii) an outcome, and (iii) a time range associated with the outcome.

At 215, control selects an outcome model associated with the received prediction request. For example, control may select an outcome model stored in the outcome model data store 130 that accepts the mutable and immutable attributes included in the received request as inputs and outputs a prediction of the outcome during the time range specified in the received prediction request. Control continues with 220, where control sets an array (Predicted_Outcomes[ ]) to NULL. Control uses Predicted_Outcomes[ ] to store the predictions outputted by the selected outcome model and the inputs associated with the prediction. Control then progress to 225.

At 225, control uses the selected outcome model and the mutable and immutable attribute values included in the received prediction request to generate a prediction. Control progresses to 230, where control stores the generated prediction. For example, control adds the generated prediction and the mutable attribute values included in the received prediction request to Predicted_Outcomes[ ]. Control continues with 235.

At 235, control generates a deviation model associated with the received prediction request. For example, control may select a plurality of values sets stored in the attribute data store 120 that correspond to the mutable and immutable attributes included in the prediction request. Control then calculates a conditional covariance matrix associated with selected value sets—for example, control may use Equation 1 to generate the conditional covariance matrix. At 235, control also sets the number of obtained samples (Sample_Count) to zero. Control then progresses to 240.

At 240, control samples the generated deviation model using the generated conditional covariance matrix. For example, control may use the mutable attribute values included in the prediction request as a mean vector associated with the generated conditional covariance matrix. At 245, control stores the generated samples by setting Current_Sample to the output of the deviation module. Control then updates the number of samples obtained by incrementing Sample_Count by one. Control progresses to 250.

At 250, control generates a prediction based on the sampled values of the deviation model (Current_Sample). For example, control uses the sampled values of the deviation model (Current_Sample) and the immutable attribute values included in the received prediction request as inputs to the selected outcome model. At 255, control stores the generated prediction. For example, control adds the output of the outcome model and Current_Sample to Predicted_Outcomes[ ]. Control then progresses to 260.

At 260, control determines whether the number of obtained samples (Sample_Count) is less than a predetermined threshold value. The predetermined threshold value represents the total number of sampled mutable attribute values to be obtained from the deviation model and used to generate a prediction. If control determines that Sample_Count is less than the predetermined threshold value, control returns to 240; otherwise, control transfers to 265. At 265, control outputs the result of the received prediction request. For example, control outputs the predictions and associated mutable attribute values stored in Prediction_Outcomes[ ].

Control continues at 270. Based on Prediction_Outcomes[ ], control may generate a message with an action recommendation for the subject. The action recommendation may include one or more actions to take to reduce a particular outcome. Control continues at 275, where control transmits the message generated at 270 in the event that the message was generated. Control then returns to 210.

Example Output

Figure 3:
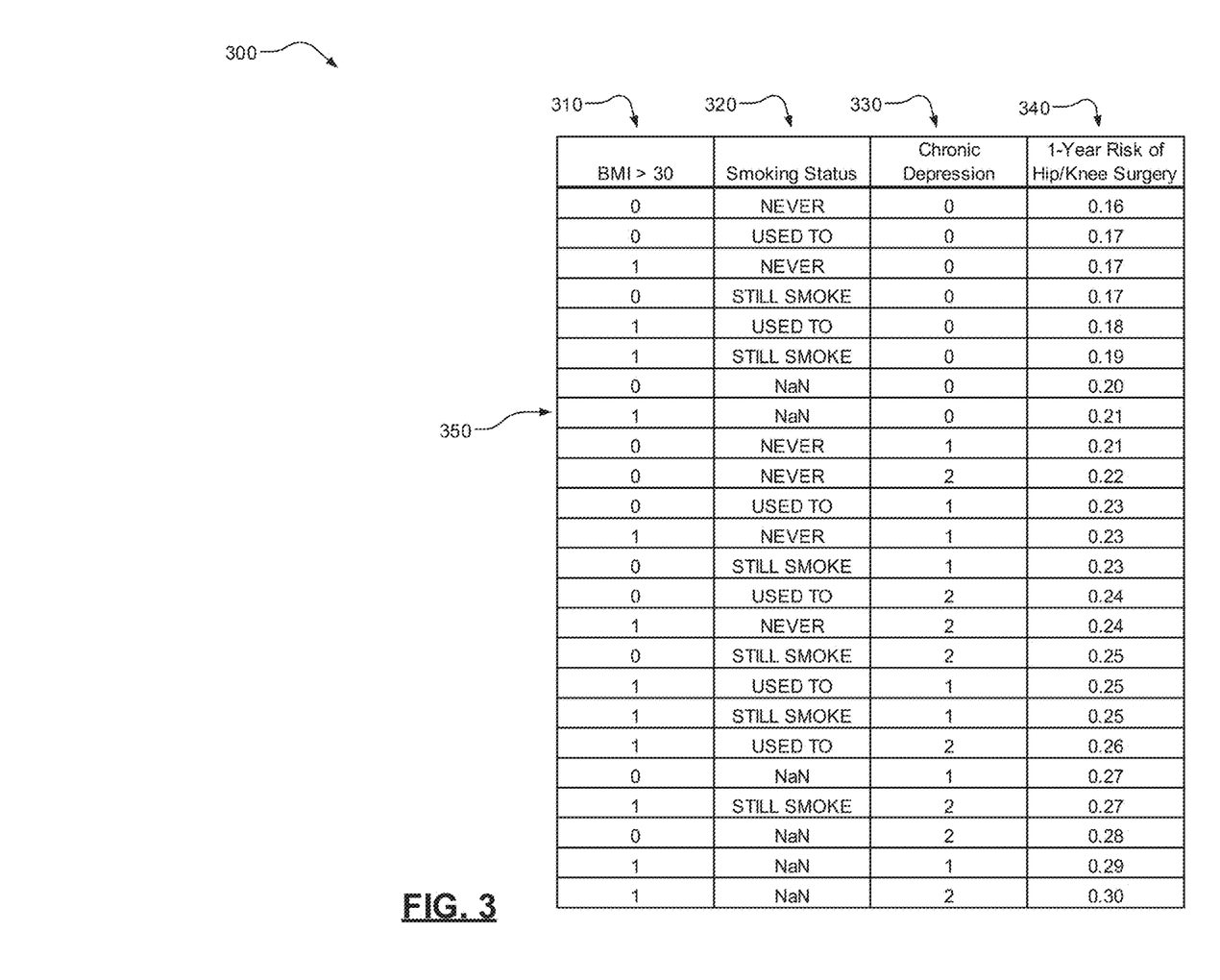
FIG. 3 is a visual depiction of an example prediction result according to the principles of the present disclosure.

In FIG. 3, a table 300 includes data from an example prediction result generated by the prediction system 105. Each row of the table 300 represents a different predicted outcome. Each predicted outcome includes a value associated with the subject's body mass index (BMI) 310, the smoking status 320 of the subject, a chronic depression value 330 associated with the subject, and a probability 340 that the subject will have hip and/or knee surgery in the next year. In the table 300, the term "NaN" stands for "not a number" and indicates that the value for an attribute—for example, smoking status—is unknown.

For a representative subject having a BMI greater than 30, unknown smoking status, and a chronic depression value of 0, the predicted risk of needing hip/knee surgery in the next year is 0.21 (21%). This representative subject corresponds to row 350 of the table 300.

BMI 310, smoking status 320, and chronic depression value 330 are mutable attributes that may affect the need for hip and/or knee surgery in the future. A reviewer, such as an automated intervention system or notification system, may use the table 300 to recommend one more actions to the subject to reduce their risk of hip and/or knee surgery in the next year. The actions are encoded in a message and transmitted to the subject.

As an example, the reviewer may suggest that the subject take the necessary actions to change their smoking status and/or BMI to match a predicted outcome that includes a lower probability 340 than the subject's current value. For example, the reviewer may suggest that the subject change their diet and exercise routine to lower their BMI below 30 to reduce their likelihood of needing hip and/or knee surgery in the next year.

Machine-Learning Models

Figure 4A:
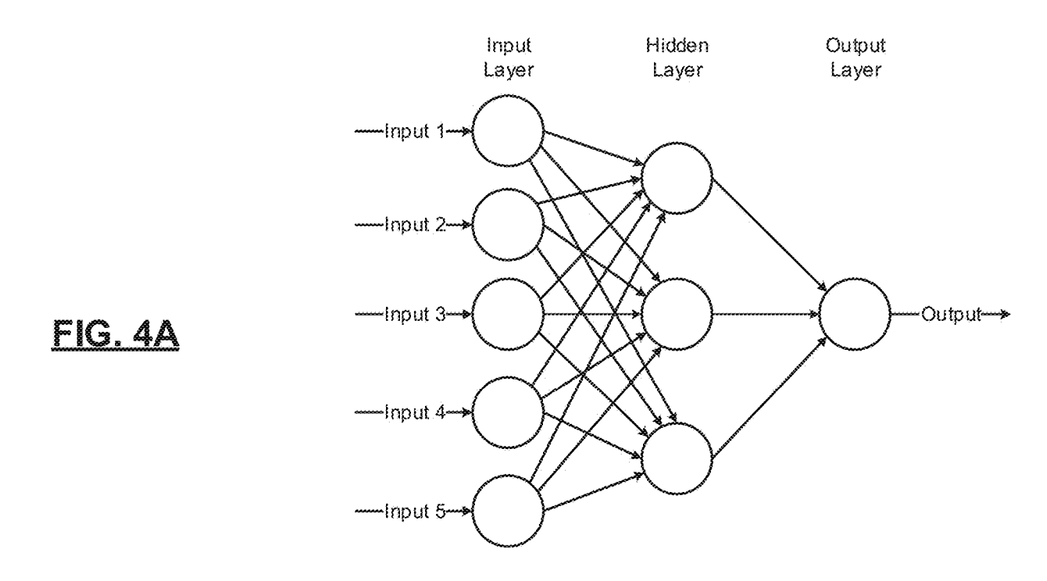
FIGS. 4A and 4B are graphical representations of an example recurrent neural network to implement machine learning models.
Figure 4B:
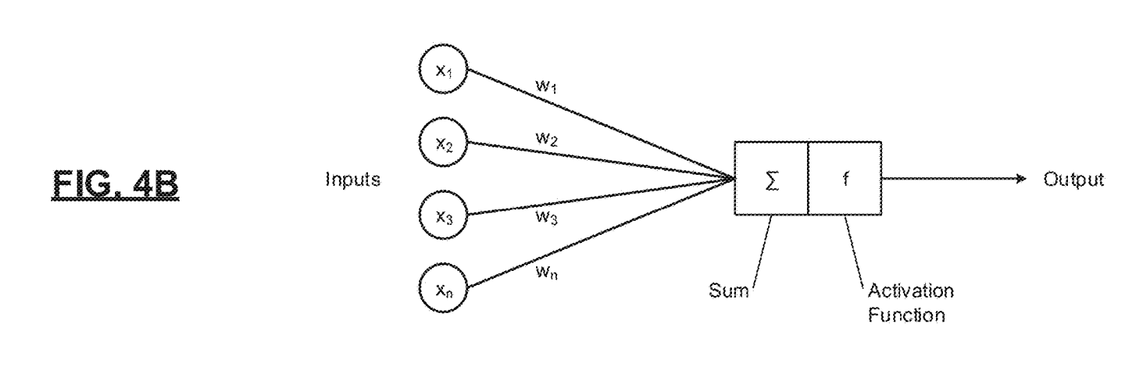

The models used by the deviation module 115 and the prediction module 125 may take the form of a recurrent neural network (RNN), such as a long short-term memory (LSTM) model. FIGS. 4A and 4B illustrate an example RNN. Machine learning is a method used to devise complex models and algorithms that lend themselves to prediction (e.g., health plan customer predictions, etc.). The models generated using machine learning can produce reliable, repeatable decisions and results, and uncover hidden insights through learning from historical relationships and trends in the data.

The purpose of using the recurrent-neural-network-based model and training the model using machine learning as described above is to directly predict dependent variables without casting relationships between the variables into mathematical form. The neural network model includes a large number of virtual neurons operating in parallel and arranged in layers. The first layer is the input layer and receives raw input data. Each successive layer modifies outputs from a preceding layer and sends them to a next layer. The last layer is the output layer and produces output of the system.

FIG. 4A shows a fully connected neural network, where each neuron in a given layer is connected to each neuron in a next layer. In the input layer, each input node is associated with a numerical value, which can be any real number. In each layer, each connection that departs from an input node has a weight associated with it, which can also be any real number (see FIG. 4B). In the input layer, the number of neurons equals number of features (columns) in a dataset. The output layer can have multiple continuous outputs.

The layers between the input and output layers are hidden layers. The number of hidden layers can be one or more (one hidden layer may be sufficient for most applications). A neural network with no hidden layers can represent linear separable functions or decisions. A neural network with one hidden layer can perform continuous mapping from one finite space to another. A neural network with two hidden layers can approximate any smooth mapping to any accuracy.

The number of neurons can be optimized. At the beginning of training, a network configuration is more likely to have excess nodes. Some of the nodes that would not noticeably affect network performance may be removed from the network during training. For example, nodes with weights approaching zero after training can be removed (this process is called pruning). The number of neurons can cause under-fitting (inability to adequately capture signals in dataset) or over-fitting (insufficient information to train all neurons; network performs well on training dataset but not on test dataset).

Various methods and criteria can be used to measure performance of a neural network model. For example, root mean squared error (RMSE) measures the average distance between observed values and model predictions. Coefficient of Determination ($R^2$) measures correlation (not accuracy) between observed and predicted outcomes (for example, between trained model outputs and actual outputs of test data). This method may not be reliable if the data has a large variance. Other performance measures include irreducible noise, model bias, and model variance. A high model bias for a model indicates that the model is not able to capture true relationship between predictors and the outcome. Model variance can indicate whether a model is not stable (a slight perturbation in the data will significantly change the model fit).

CONCLUSION

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

The invention claimed is:

1. A computer-implemented method comprising:
   maintaining an attribute data store that includes a plurality of sets of values for mutable attributes and immutable attributes;
   maintaining a set of outcome models, wherein each outcome model of the set of outcome models is a neural network that generates a predicted likelihood of a respective outcome in response to at least one immutable attribute value and at least one mutable attribute value, and wherein each neural network includes:
     an input layer having a plurality of input nodes,
     one or more hidden layers having a plurality of hidden nodes, and
     an output layer having one or more output nodes,
     wherein inputs are provided from the input nodes to at least one of the hidden nodes, the hidden layers modify the inputs, and the hidden layers send the modified outputs to the output layer;
   receiving, at an outcome generation module, a prediction request that specifies a first outcome, a set of values for at least one immutable attribute, and a set of values for at least one mutable attribute; and
   in response to the prediction request:
     selecting, at a deviation module, a group of sets from the plurality of sets of the attribute data store, wherein each set in the group of sets has values for the immutable attributes that match the set of values for the at least one immutable attribute in the prediction request;
     determining, at the deviation module, a conditional covariance matrix for the group of sets;
     generating, at the deviation module, a deviation model based on the conditional covariance matrix;
     sampling, at the deviation module, the deviation model to generate a plurality of sets of likely mutable attribute values;
     receiving, at a prediction module, at least one of the sets of likely mutable attribute values;
     automatically selecting, at the prediction module, one of the neural networks from the set of outcome models based on the at least one set of likely mutable attribute values;
     for each of a subset of the plurality of sets of mutable attribute values, generating a respective likelihood of the first outcome occurring at the prediction module using the selected neural network, the set of values for the at least one immutable attribute of the prediction request, and the at least one set of likely mutable attribute values;
     based on the respective likelihoods, selectively generating a message with an action recommendation; and
     automatically transmitting the message to a user associated with the prediction request.

2. The method of claim 1 wherein:
   the conditional covariance matrix is calculated according to:
   $$\hat{\Sigma}_a = \Sigma_a - \Sigma_c \Sigma_b^{-1} \Sigma_c^T;$$
   $\hat{\Sigma}_a$ is the conditional covariance matrix;
   $\Sigma_a$ is a covariance matrix associated with the values for the mutable attributes in the group of sets;
   $\Sigma_b^{-1}$ is an inverse of a covariance matrix associated with the values for the immutable attributes in the group of sets;
   $\Sigma_c$ is a covariance matrix of the values for the mutable attributes in the group of sets crossed with the values for the immutable attributes in the group of sets; and
   $\Sigma_c^T$ is the transpose of $\Sigma_c$.

3. The method of claim 1 wherein the subset is increased until a predetermined number is reached.

4. The method of claim 1 wherein the deviation model is generated based on the conditional covariance matrix as well as a mean mutable values vector.

5. The method of claim 4 wherein the set of values for the at least one mutable attribute of the prediction request is used as the mean mutable values vector.

6. The method of claim 4 wherein the deviation model represents a multivariate Gaussian distribution.

7. The method of claim 1 wherein the first outcome is a medical outcome including at least one of a medical diagnosis or a prescribed procedure.

8. The method of claim 1 wherein:
   each of the plurality of sets of values includes a time horizon;
   the prediction request includes a first time horizon; and
   for each set in the group of sets, the time horizon corresponds to the first time horizon.

9. The method of claim 8 wherein each outcome model of the set of outcome models generates the predicted likelihood of the respective outcome in response to the at least one immutable attribute value, the at least one set of likely mutable attribute value, and the time horizon.

10. The method of claim 8 wherein the time horizon is measured in months.

11. The method of claim 1 wherein:
    the immutable attributes include age and
    the mutable attributes include at least one of body mass index (BMI), tobacco usage, cholesterol level, and VO2 max.

12. The method of claim 1 wherein the selected outcome model is selected according to the first outcome of the prediction request.

13. A system comprising:
    memory hardware configured to store instructions and
    processing hardware configured to execute the instructions stored by the memory hardware,
    wherein the instructions include:
    maintaining an attribute data store that includes a plurality of sets of values for mutable attributes and immutable attributes;
    maintaining a set of outcome models, wherein each outcome model of the set of outcome models is a neural network that generates a predicted likelihood of a respective outcome in response to at least one immutable attribute value and at least one mutable attribute value, and wherein each neural network includes:
an input layer having a plurality of input nodes,
one or more hidden layers having a plurality of hidden nodes, and
an output layer having one or more output nodes,
wherein inputs are provided from the input nodes to at least one of the hidden nodes, the hidden layers modify the inputs, and the hidden layers send the modified outputs to the output layer;

receiving, at an outcome generation module, a prediction request that specifies a first outcome, a set of values for at least one immutable attribute, and a set of values for at least one mutable attribute; and in response to the prediction request:
selecting, at a deviation module, a group of sets from the plurality of sets of the attribute data store, wherein each set in the group of sets has values for the immutable attributes that match the set of values for the at least one immutable attribute in the prediction request;
determining, at the deviation module, a conditional covariance matrix for the group of sets;
generating, at the deviation module, a deviation model based on the conditional covariance matrix;
sampling, at the deviation module, the deviation model to generate a plurality of sets of likely mutable attribute values;
receiving, at a prediction module, at least one of the sets of likely mutable attribute values;
automatically selecting, at the prediction module, one of the neural networks from the set of outcome models based on the at least one set of likely mutable attribute values;
for each of a subset of the plurality of sets of mutable attribute values, generating a respective likelihood of the first outcome occurring at the prediction module using the selected neural network, the set of values for the at least one immutable attribute of the prediction request, and the at least one set of likely mutable attribute values;
based on the respective likelihoods, selectively generating a message with an action recommendation; and
automatically transmitting the message to a user associated with the prediction request.

14. The system of claim 13 wherein:
the conditional covariance matrix is calculated according to:

$$\hat{\Sigma}_a = \Sigma_a - \Sigma_c \Sigma_b^{-1} \Sigma_c^T;$$

$\hat{\Sigma}_a$ is the conditional covariance matrix;
$\Sigma_a$ is a covariance matrix associated with the values for the mutable attributes in the group of sets;
$\Sigma_b^{-1}$ is an inverse of a covariance matrix associated with the values for the immutable attributes in the group of sets;
$\Sigma_c$ is a covariance matrix of the values for the mutable attributes in the group of sets crossed with the values for the immutable attributes in the group of sets; and
$\Sigma_c^T$ is the transpose of $\Sigma_c$.

15. The system of claim 13 wherein:
the deviation model is generated based on the conditional covariance matrix as well as a mean mutable values vector and
the deviation model represents a multivariate Gaussian distribution.

16. The system of claim 15 wherein the set of values for the at least one mutable attribute of the prediction request is used as the mean mutable values vector.

17. The system of claim 13 wherein:
each of the plurality of sets of values includes a time horizon;
the prediction request includes a first time horizon; and
for each set in the group of sets, the time horizon corresponds to the first time horizon.

18. The system of claim 17 wherein each outcome model of the set of outcome models generates the predicted likelihood of the respective outcome in response to the at least one set of likely immutable attribute value, the at least one mutable attribute value, and the time horizon.

19. A non-transitory computer-readable medium storing processor-executable instructions comprising:
maintaining an attribute data store that includes a plurality of sets of values for mutable attributes and immutable attributes;
maintaining a set of outcome models, wherein each outcome model of the set of outcome models is a neural network that generates a predicted likelihood of a respective outcome in response to at least one immutable attribute value and at least one mutable attribute value, wherein each neural network includes:
an input layer having a plurality of input nodes,
one or more hidden layers having a plurality of hidden nodes, and
an output layer having one or more output nodes,
wherein inputs are provided from the input nodes to at least one of the hidden nodes, the hidden layers modify the inputs, and the hidden layers send the modified outputs to the output layer;

receiving, at an outcome generation module, a prediction request that specifies a first outcome, a set of values for at least one immutable attribute, and a set of values for at least one mutable attribute; and in response to the prediction request:
selecting, at a deviation module, a group of sets from the plurality of sets of the attribute data store, wherein each set in the group of sets has values for the immutable attributes that match the set of values for the at least one immutable attribute in the prediction request;
determining, at the deviation module, a conditional covariance matrix for the group of sets;
generating, at the deviation module, a deviation model based on the conditional covariance matrix;
sampling, at the deviation module, the deviation model to generate a plurality of sets of likely mutable attribute values;
receiving, at a prediction module, at least one of the sets of likely mutable attribute values,
automatically selecting, at the prediction module, one of the neural networks from the set of outcome models based on the at least one set of likely mutable attribute values;
for each of a subset of the plurality of sets of mutable attribute values, generating a respective likelihood of the first outcome occurring at the prediction module using the selected neural network, the set of values for the at least one immutable attribute of the prediction request, and the at least one set of likely mutable attribute values;
based on the respective likelihoods, selectively generating a message with an action recommendation; and automatically transmitting the message to a user associated with the prediction request.

20. The computer-readable medium of claim 19 wherein:
the conditional covariance matrix is calculated according to:

$$\hat{\Sigma}_a = \Sigma_a - \Sigma_c \Sigma_b^{-1} \Sigma_c^T;$$

$\hat{\Sigma}_a$ is the conditional covariance matrix;
$\Sigma_a$ is a covariance matrix associated with the values for the mutable attributes in the group of sets;
$\Sigma_b^{-1}$ is an inverse of a covariance matrix associated with the values for the immutable attributes in the group of sets;
$\Sigma_c$ is a covariance matrix of the values for the mutable attributes in the group of sets crossed with the values for the immutable attributes in the group of sets; and
$\Sigma_c^T$ is the transpose of $\Sigma_c$.

\* \* \* \* \*